United States Patent
Ekelius et al.

(12) 
(10) Patent No.: US 6,637,431 B2
(45) Date of Patent: Oct. 28, 2003

(54) INHALATION DEVICE EMPLOYING BLISTER PACKS WITH CAVITIES AND ALIGNMENT SLITS

(75) Inventors: Carina Ekelius, Vellinge (SE);
Per-Åke Ohlsson, Staffanstorp (SE);
Anders Selmer, Skurup (SE)

(73) Assignee: AstraZeneca AB, Sodertalje (SE)

(*) Notice: Subject to any disclaimer, the term of this patent is extended or adjusted under 35 U.S.C. 154(b) by 54 days.

(21) Appl. No.: 09/830,237

(22) PCT Filed: Dec. 21, 2000

(86) PCT No.: PCT/SE00/02649
§ 371 (c)(1),
(2), (4) Date: Apr. 24, 2001

(87) PCT Pub. No.: WO01/45634
PCT Pub. Date: Jun. 28, 2001

(65) Prior Publication Data
US 2002/0124846 A1 Sep. 12, 2002

(30) Foreign Application Priority Data
Dec. 21, 1999 (SE) .................................. 9904706

(51) Int. Cl.⁷ .................... A61M 15/00; A62B 7/00; A61J 1/03
(52) U.S. Cl. ................ 128/203.15; 128/203.21; 221/25; 206/532; 206/538; 206/828
(58) Field of Search .............. 128/203.15, 203.21, 128/203.23, 203.12, 203.18, 203.19; 206/438, 531, 536, 538, 540, 828, 532; 221/25, 31; 222/81–83, 87; 604/58

(56) References Cited

U.S. PATENT DOCUMENTS

| | | |
|---|---|---|
| 4,294,361 A | 10/1981 | Margulies et al. |
| 5,088,603 A | 2/1992 | Kirkpatrick |
| 5,533,502 A | 7/1996 | Piper |

FOREIGN PATENT DOCUMENTS

| | | |
|---|---|---|
| DE | 19757207 | 6/1999 |
| EP | 4128342 | 3/1996 |
| WO | WO 99/31952 | 7/1996 |
| WO | WO 97/40676 | 11/1997 |

OTHER PUBLICATIONS

International Search Report of PCT/SE00/02649.

*Primary Examiner*—Henry Bennett
*Assistant Examiner*—Kathryn Ferko
(74) *Attorney, Agent, or Firm*—Fish & Richardson P.C.

(57) ABSTRACT

The present invention relates to a blister pack (12) having a plurality of blisters (13) each holding a dose of a powdered medicament comprising a lower base (18) containing a plurality of cavities (19) for the powdered medicament and an upper sealing foil layer (20) which covers the lower base (18) to form the blisters (13). Each cavity (19) is provided with at least one adjacent slit (21) formed by scoring the foil layer (20) and a lower base (18). The slit (21) ensuring accurate penetration of a cavity (19) by a suction tube through which a user can inhale the contents of the cavity (19).

11 Claims, 17 Drawing Sheets

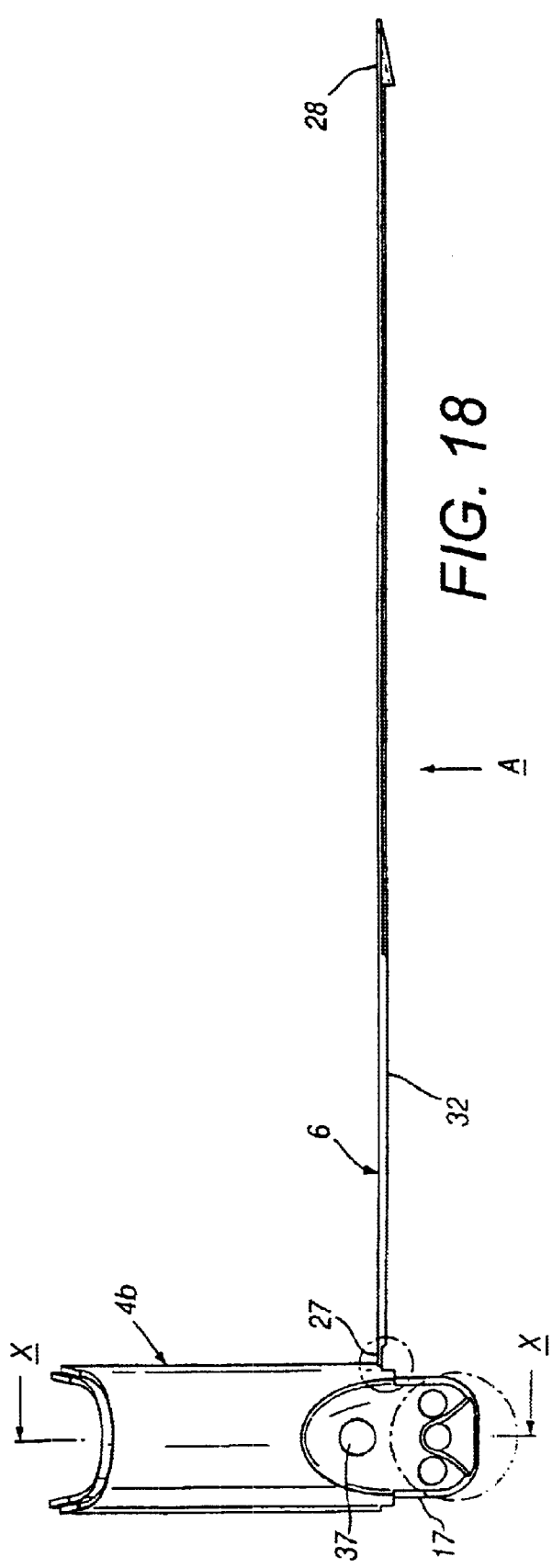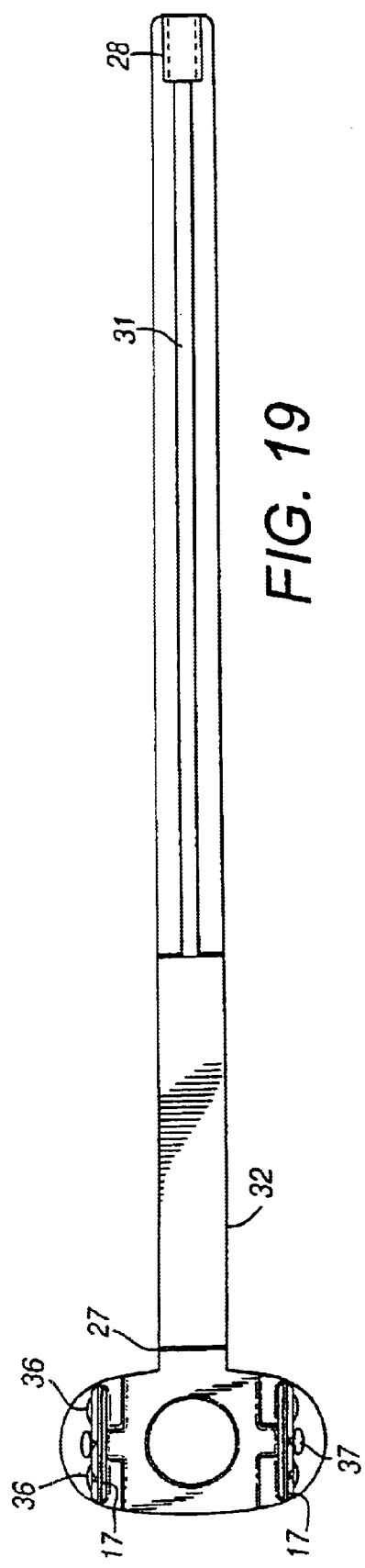

INHALATION DEVICE EMPLOYING BLISTER PACKS WITH CAVITIES AND ALIGNMENT SLITS

The present invention relates to an inhalation device, in particular, an inhalation device for administering a powdered medicament by inhalation from a blister pack.

It is known in the treatment of respiratory conditions to make use of dry powder inhalers comprising a suction tube arranged so that it is able to cooperate with a blister pack containing a plurality of individual blisters each holding a dose of powdered medicament.

Reference should now be made to WO 97/40876 which discloses an inhalation device comprising a suction tube and a blister pack assembly. The blister pack assembly is in the form of a carrier which holds the blister pack. The carrier is configured such that the upper surface has a plurality of holes which sit above the blisters in the blister pack thereby enabling the distal end of the suction tube to penetrate the blisters as and when required.

The object of the present invention is to provide an improved inhalation device of this kind which has a superior construction and is more user-friendly. In particular, the construction should be light and compact whilst retaining sufficient rigidity and strength bearing in mind that the user may have to administer the powdered medicament at frequent intervals. Moreover, the construction should be such that the user cannot misuse the inhalation device since incorrect delivery of the powdered medicament could be potentially harmful to the user.

According to the present invention, there is provided a blister pack having a plurality of blisters each holding a dose of a powdered medicament comprising a lower base containing a plurality of cavities for the powdered medicament and an upper sealing foil layer which covers the lower base to form the blisters, wherein each cavity is provided with at least one adjacent slit formed by scoring the foil layer and lower base, the slit ensuring accurate penetration of a cavity by a suction tube through which a user can inhale the contents of the cavity.

Preferably, the opposed edges of a slit are folded back towards the lower base to facilitate penetration by the suction tube.

Preferably, a scored slit sits at a distance of approximately 2 mm from the cavity perimeter.

In a further aspect, the present invention also provides a blister pack assembly comprising the blister pack and a carrier for the blister pack.

Preferably, the carrier comprises an upper tray and a lower tray which are interconnectable around the blister pack, the upper tray being provided with a plurality of holes and slots which sit above and correspond with the positions of the cavities and slits in the blister pack.

Preferably, the lower tray is provided with a plurality of slots which sit below and correspond with the slits in the blister pack.

In yet a further aspect, the present invention provides an inhalation device comprising the blister pack assembly and a suction tube which is constructed for cooperation with the blister pack assembly having a distal end which can penetrate the foil above a cavity, a proximal end through which the user inhales and at least one guide arm which accurately locates the distal end of the suction tube in a cavity by penetrating the blister pack assembly.

Preferably, the guide arm or arms have a tapered configuration to facilitate location in the blister pack assembly.

Preferably, the suction tube is removably hinged to the carrier by way of cooperating elements on the guide arm or arms and the carrier.

Preferably, the guide arm or arms are provided with a shallow channel which facilitates relocation of the suction tube on the hinge.

Preferably, the distal end of the suction tube is constructed to ensure there is an air gap between the suction tube and the blister pack assembly when the suction tube penetrates a blister.

A preferred embodiment of the present invention will now be described, by way of example only, with reference to the accompanying drawings, of which:

FIG. 18 is a view from one side of the external sleeve and resilient strip in FIG. 17;

FIG. 19 is a view in direction A in FIG. 18;

FIGS. 20b and 20c depict an alternative configuration for the guide arm shown in FIG. 20a;

Figure 1:
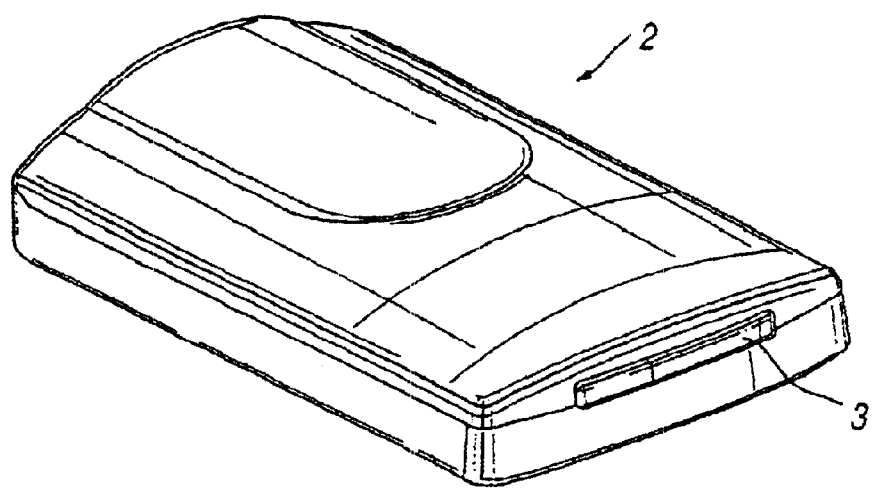
FIG. 1 is a perspective view of a preferred embodiment of the inhalation device when enclosed in an outer case.
Figure 2:
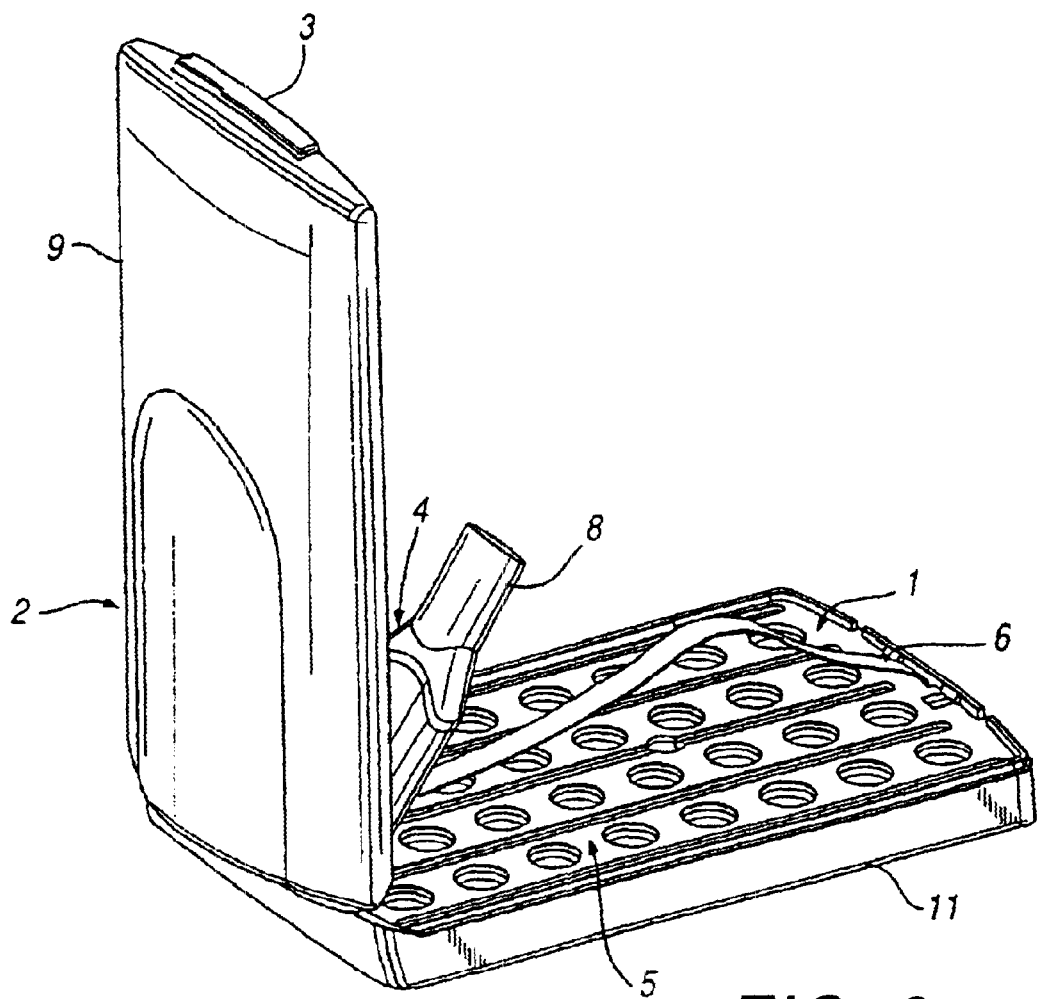
FIG. 2 is a perspective view of the inhalation device in FIG. 1 when the outer case has been opened.
Figure 3:
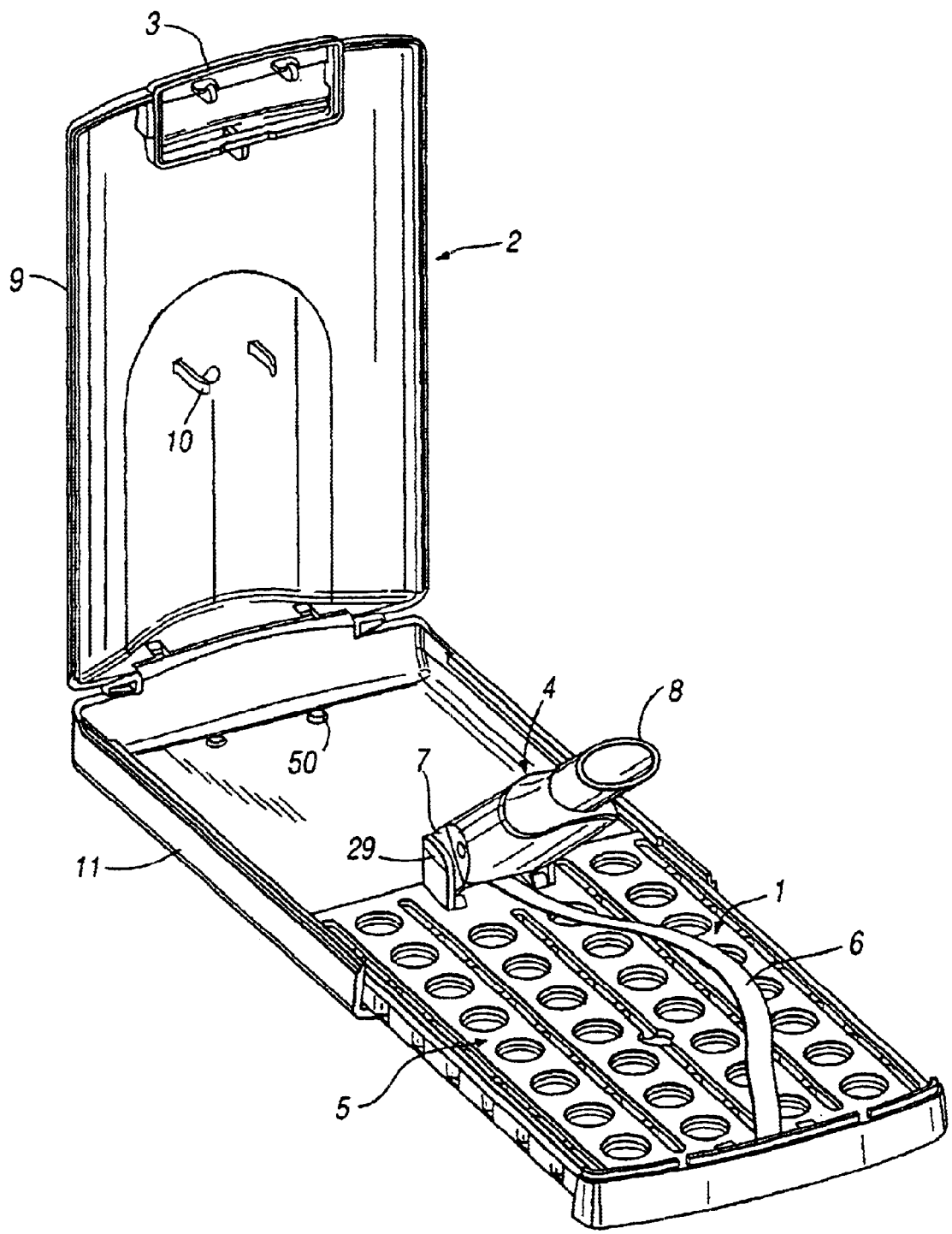
FIG. 3 is a perspective view of the inhalation device in FIG. 2 showing how the suction tube and blister pack assembly are inserted into the outer case.
Figure 4:
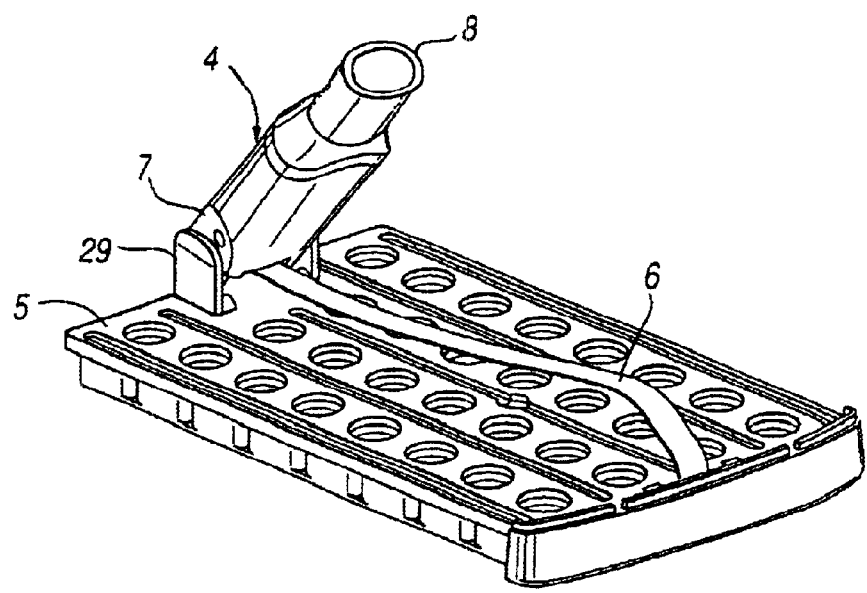
FIG. 4 is a perspective view of the inhalation device when removed from the outer case.

Reference should now be made to FIGS. 1, 2 and 3 which are various perspective views of a first preferred embodiment of the inhalation device 1 when enclosed in an outer case 2. The outer case 2 is hinged having a typical push-button locking mechanism 3. FIG. 4 depicts the inhalation device 1 when removed from the outer case 2. The outer case 2 is constructed such that the inhalation device 1 can slide into the base 11. The sides of the blister pack assembly 5 cooperate with the internal surface of the sides of the base 11 to ensure that the inhalation device 1 is held securely in the outer case 2. In addition, the base 11 has two latching elements 50 which cooperate with holes 51 in the lower tray 16 (see FIG. 27) which further secure the inhalation device 1 in the outer case 2.

The inhalation device 1 comprises a suction tube 4 and a blister pack assembly 5. The suction tube 4 is removably connected to the blister pack assembly 5 by an elongate resilient strip 6 which biases the suction tube 4 away from the blister pack assembly 5. The resilient strip 6 is constructed such that when the outer case 2 is closed the suction tube 4 can lie substantially flat against the blister pack assembly 5. On opening the outer case 2, the resilient strip 6 will raise the suction tube 4 such that it can be easily grasped by a user.

The suction tube 4 is hinged on the blister pack assembly 5. The internal surface of the lid 9 of the outer case 2 can optionally be provided with arms 10 which interlock in a snap-action with the proximal end 8 of the suction tube 4 when the outer case 2 is closed. On opening the outer case 2, the arms 10 will cooperate with the resilient strip 6 to raise the suction tube 4. The arms 10 are constructed to slip over the proximal end 8 of the suction tube 4 as the lid 9 is rotated away from the blister pack assembly 5 and eventually release the proximal end 8, at which point the resilient strip 6 continues to maintain the suction tube 4 in the raised position.

In FIG. 3, it is clear how the inhalation device 1 can slide into the base 11 of the outer case 2. The suction tube 4 and blister pack assembly 5 can be removed and replaced when the user has emptied all the blisters 13 in the blister pack 12 seen in the exploded view in FIG. 5.

The blister pack assembly 5 comprises a carrier 14 and the blister pack 12. The carrier 14 has an upper tray 15 and a lower tray 16 which interlock and enclose the blister pack 12.

Figure 6:
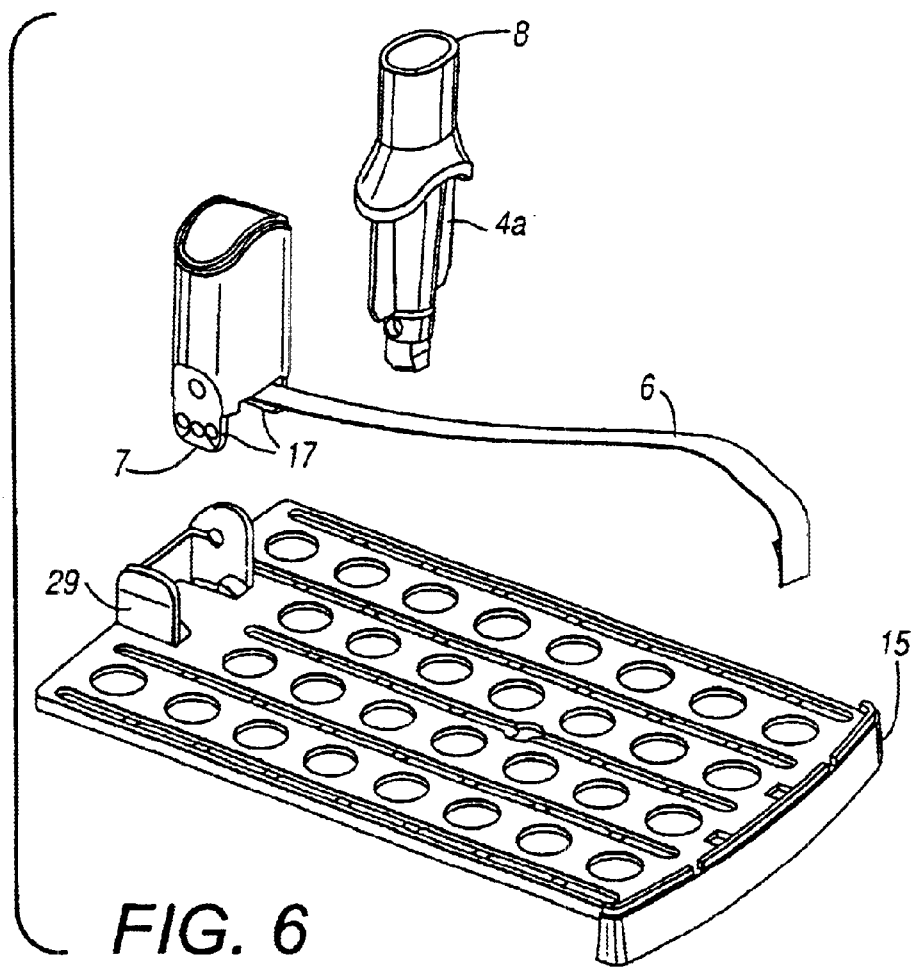
FIG. 6 is an exploded view of the elements attached to the upper tray of the blister pack assembly.

In FIG. 6, the elements attached to the upper tray 15 have been exploded. Suction tube 4 comprises a body 4a and an external sleeve 4b. However, the suction tube 4 can be moulded as a single part rather than as two separate elements. The body 4a includes the proximal end 8 which forms the mouthpiece of the suction tube 4. The external sleeve 4b includes the distal end 7 and comprises guide arms 17 which hinge the suction tube 4 to the upper tray 15 and facilitate location of the suction tube 4 in the blister pack assembly 5.

Figure 7:
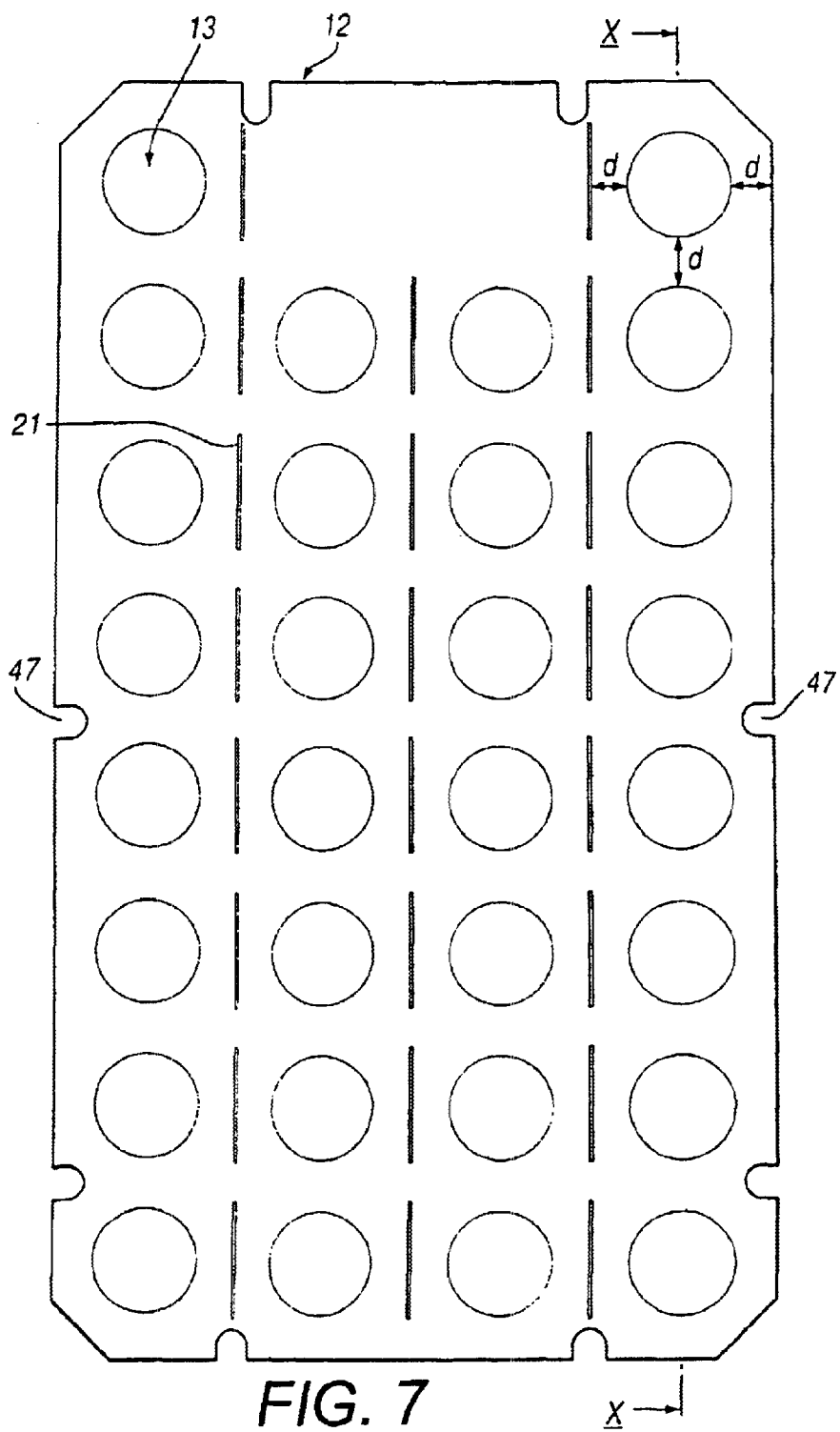
FIG. 7 is a plan view of the blister pack in FIG. 5.
Figure 8:
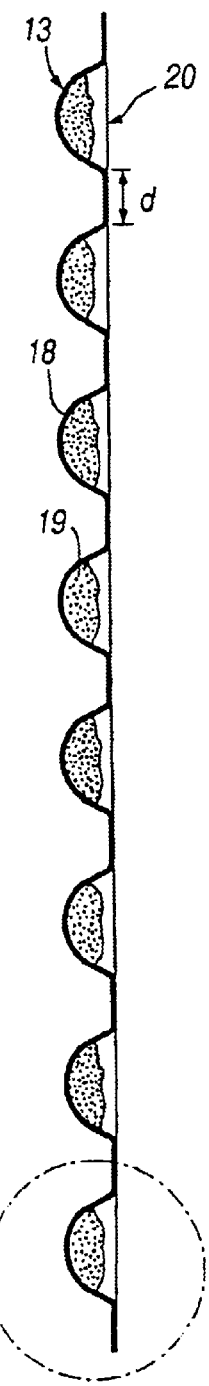
FIG. 8 is a sectional view in direction X—X of the blister pack in FIG. 7.
Figure 9:
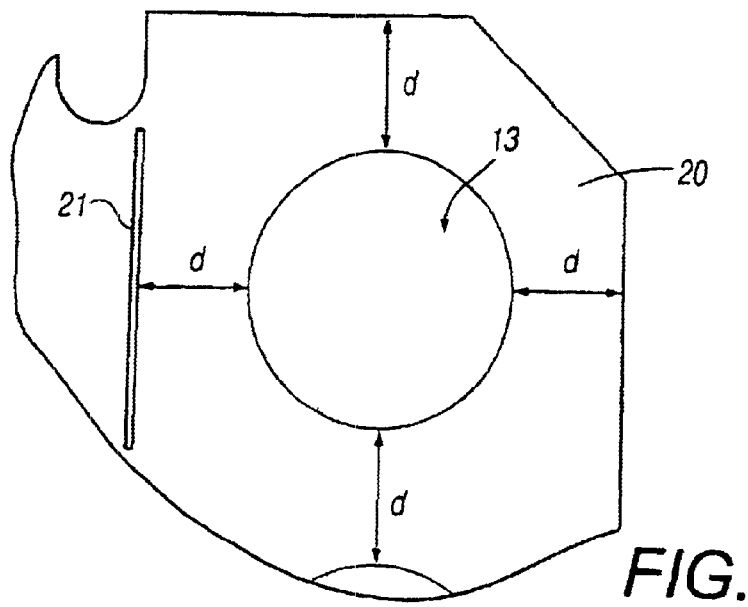
FIG. 9 shows the detail of a single blister and slit in plan view.
Figure 10:
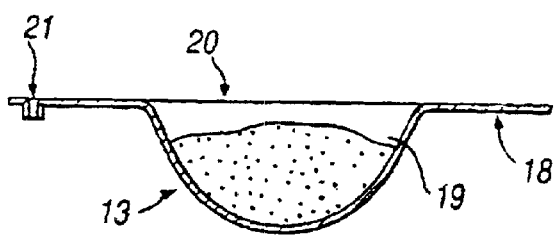
FIG. 10 is a sectional view through the blister and slit in FIG. 9 (with a modified slit)

FIG. 7 is a plan view of the blister pack 12. The blister pack 12 has a plurality of blisters 13 arranged in four parallel rows. Each blister 13 holds a dose of powdered medicament (visible in FIGS. 8 and 10). The blister pack 12 comprises a lower base 18 containing a plurality of cavities 19 and an upper foil layer 20 which is sealed to the lower base 18. There is an optimum minimum sealing distance around a blister 13 in order to ensure that there will be no or very little ingress of moisture within a cavity 19 which could contaminate or degrade the powdered medicament. The sealing distance "d" from the edge of a cavity 19 to the edge of an adjacent cavity 19 or a cut edge of the blister pack 12 must typically be at least 2 mm. With this minimum sealing distance in mind, the aim is to reduce the overall size of the blister pack 12 for a given number of blisters 13. However, the blister pack 12 must also allow penetration of the guide arms 17 of the suction tube 4 on each side of a blister 13 and, therefore, the foil layer 20 and lower base 18 must be cut during manufacture of the blister pack 12. Although the blister pack 12 could be cut by removing appropriately shaped slots from the blister pack 12, there is the complication of removal of the cut portions of foil and base material. Any cut portions which are not removed could fall into a cavity, sit above a blister or affect the sealing of the foil to the base material. Furthermore, if a slot is cut away from the foil and base material the overall size of the blister pack 12 would have to increase bearing in mind the minimum sealing distance "d" of 2 mm and any additional width of the slot.

Accordingly, the blister pack 12 is provided with slits 21 which are simply formed by scoring both the foil layer 20 and lower base 18. In this way, the minimum sealing distance "d" of 2 mm can be achieved without adding to the overall size of the blister pack 12.

Although the guide arms 17 are constructed such that penetration of the slits 21 requires little force by the user, insertion can be facilitated by folding the opposed edges of the scored foil and base material downwardly to increase the width of the slit 21 without affecting the minimum sealing distance "d". The optional folding of the opposed edges of the slit 21 can be seen in FIG. 10 and FIG. 41. Alternatively, the guide arms 17 can be constructed such that they have a narrower profile than the slit 21.

Figure 11:
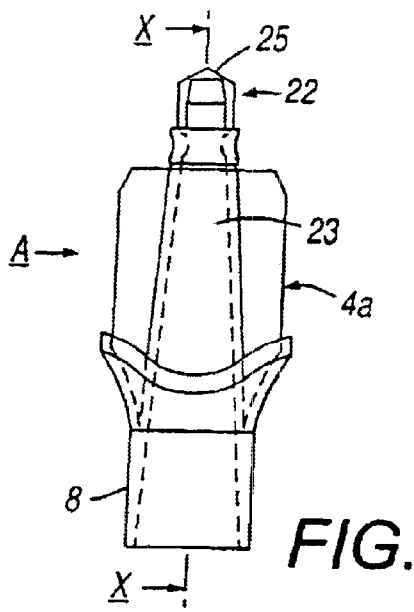
FIG. 11 is a view of one side of the body of the suction tube.

The detailed construction of the suction tube 4 will now be described with reference to FIGS. 11 to 23. In FIG. 11 the body 4a of the suction tube is depicted. The body 4a comprises a mouthpiece 8 which forms the proximal end of the suction tube and a cutting mechanism 22 at the opposite end. A tapered channel 23 runs from the mouthpiece 8 to the cutting mechanism 22.

Figure 12:
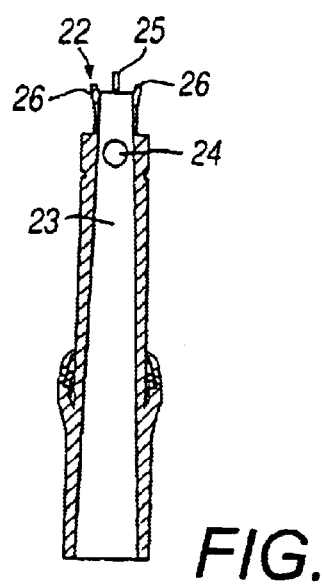
FIG. 12 is a sectional view in direction X—X in FIG. 11.
Figure 13:
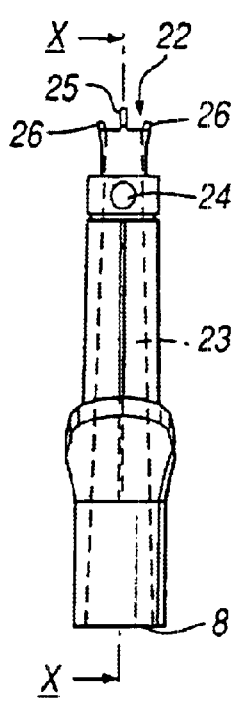
FIG. 13 is a view of the body of the suction tube in direction A in FIG. 11.
Figure 14:
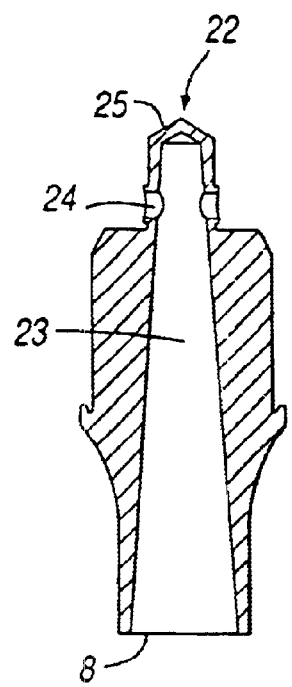
FIG. 14 is a sectional view in direction X—X in FIG. 13.
Figure 15:
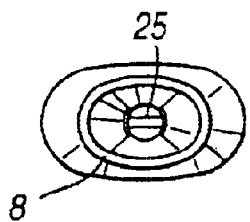
FIG. 15 is a view from above of the proximal end of the body of the suction tube in FIG. 11.
Figure 16:
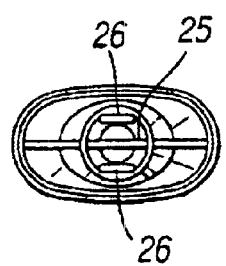
FIG. 16 is a view from below of the distal end of the body of the suction tube in FIG. 11.
Figure 17:
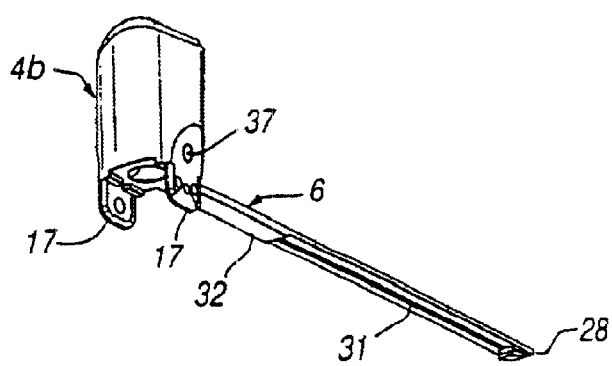
FIG. 17 is a perspective view of the external sleeve of the suction tube and resilient strip.

The cutting mechanism 22 is constructed to penetrate the foil layer 20 above a cavity 19 and allow the user to inhale the powdered medicament by breathing in through the mouthpiece 8. FIG. 12 is a sectional view in direction X—X in FIG. 11 and depicts by-pass holes 24 which will allow an additional air flow to the main air flow from within the cavity 19. FIGS. 13 and 14 are additional views of the suction tube body 4a. The cutting mechanism 22 including a cutting blade 25 and plunger blades 26 on either side of the cutting blade 25. The cutting blade 25 will actually penetrate the foil layer 20, whilst the plunger blades 26 act to push the cut foil away to create a clear passage for the powdered medicament and ensure that all the powdered medicament can be inhaled from the cavity 19.

Details of the extern-al sleeve 4b of the suction tube 4 and the resilient strip 6 can be seen in FIGS. 17 to 23.

Figure 5:
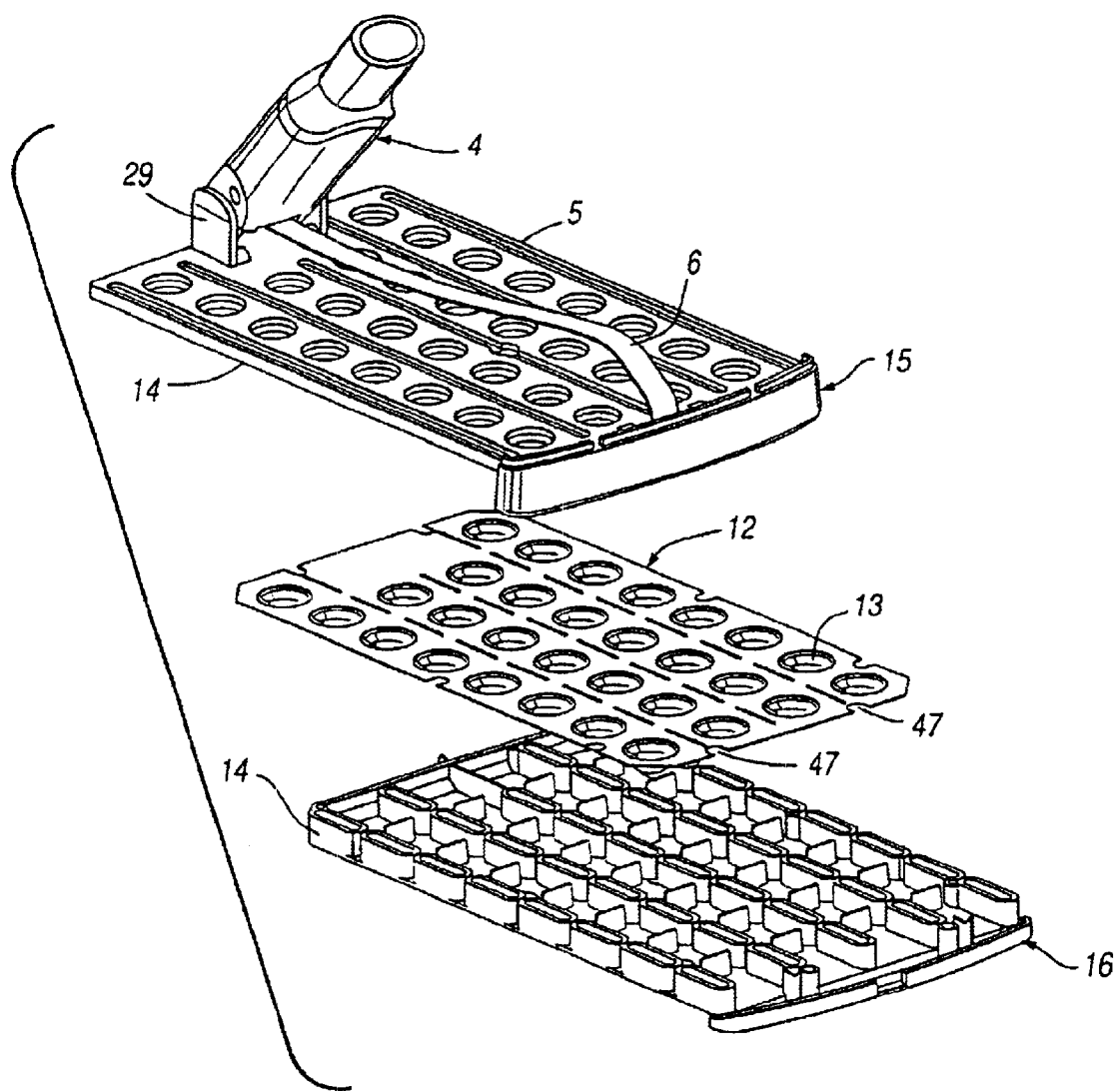
FIG. 5 is an exploded view of the elements of the inhalation device in FIG. 4.

The body 4a slots within the external sleeve 4b forming the suction tube 4 (see FIGS. 5 and 6). The resilient strip 6 has a fixed connection 27 at one end to the distal portion 7 of the suction tube 4 and is connectable by a hook 28 to the upper tray 15 at the opposite end to the hinging point of the suction tube 4 on the carrier (see FIGS. 3 and 24). The length of the resilient strip 6 is such that when the suction tube 4 sits on the hinge arms 29 and the hook 28 is located in the recess 30 in the upper tray 15, the resilient strip 6 will bend upwardly in an arc. This configuration of the resilient strip 6 results in the suction tube 4 being raised on the hinge arms 29. However, the resilient strip is sufficiently flexible to allow the suction tube 4 to pivot on the hinge into the position where it will lie substantially flat against the upper tray 15 when the outer case 2 is closed.

In FIGS. 18 and 19 further details of the guide arms 17 and resilient strip 6 are visible. The resilient strip 6 has a protruding spine 31 which gives the resilient strip 6 a shallow "T" shaped cross-section. The protruding spine 31 is on the underside of the resilient strip 6 and serves to ensure that the resilient strip 6 will arc away from the surface of the upper tray 15. The arcing of the resilient strip 6 will result due to shrinkage effects after the moulding of the plastic material from which the strip is made. There is also a thickened portion 32 adjacent to the fixed connection 27 which serves to ensure that the resilient strip 6 does not easily twist or obstruct the slots and holes in the upper tray 15 during use.

Reference should now be made to FIGS. 20 to 23 which show details of the guide arms 17 on the external sleeve 4b of the suction tube 4.

Figure 20A:
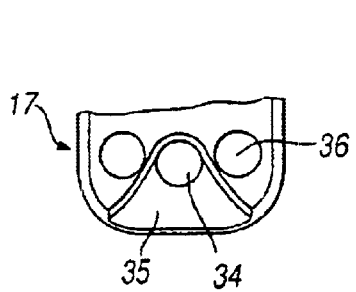
FIG. 20a shows detail of the guide arm of the suction tube in FIG. 18.

In FIG. 20a the external surface of a guide arm 17 is depicted. This surface pivots on a hinge arm 29 on the upper tray 15. In this configuration of the inhalation device, the hinge arms 29 are provided with a stub 33 and the guide arms 17 are each provided with a cooperating hole 34. In order to facilitate location of the guide arms 17 on the hinge arms 29, each guide arm 17 has a shallow tapering channel 35 leading from the outer edge of the guide arm 17 to the hole 34. The channels 35 help to re-locate the suction tube 4 on the hinge arms 29 after each use of the inhalation device. Preferably, the stubs 33 are a snap-fit in the holes 34.

Each guide arm 17 is also provided with two buttons 36 which are constructed to be a snap-fit in the slots in the upper tray 15 and lower tray 16 (described in detail with reference to FIGS. 31 to 37).

Figure 20B:
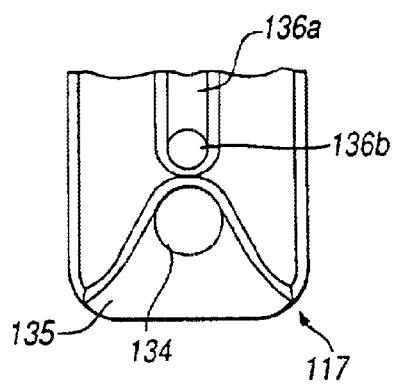
Figure 20C:
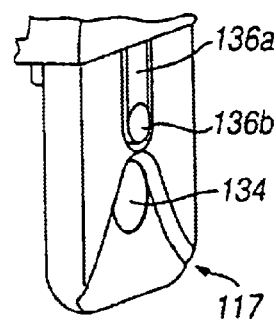
Figure 22:
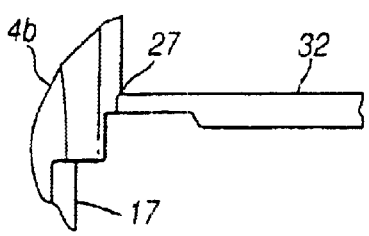
FIG. 22 shows detail of the connection of the resilient strip to the external sleeve of the suction tube.

FIGS. 20b and 20c depict an alternative configuration for the guide arm 117. Each guide arm still has a hole 134 which will cooperate with a stub 33 on the hinge arm 29 and there is a shallow tapering channel 135 to help re-locate the suction tube 4 on the hinge arms 29 after use of the inhalation device. However, a flexible leg 136a replaces the buttons 36 shown in FIG. 20a. The flexible leg 136a has a button 136b which will be a snap-fit in the slots in the upper tray 15 and lower tray 16 of the carrier 14. This alternative configuration attempts to overcome the problem of wear of the buttons 36 which can occur when the guide arms are constructed of certain materials, in particular, those which are not flexible enough. Wear of the buttons 36 will reduce the snap-fit action and result in less stability when the suction tube 4 sits in the blister pack assembly 5 during penetration of a blister. The flexible leg 136a overcomes this problem because the resilient force can be adjusted. This increase in flexibility also means that a larger button 136b can be used which also improves the snap-action. It follows that if the material from which the guide arms 117 are made is the same as the material from which the hinge arms 29 are made, the stubs 33 and holes 134 can also be increased in size to improve the snap-action of the suction tube 4 when replaced on the hinge arms 29.

Figure 21:
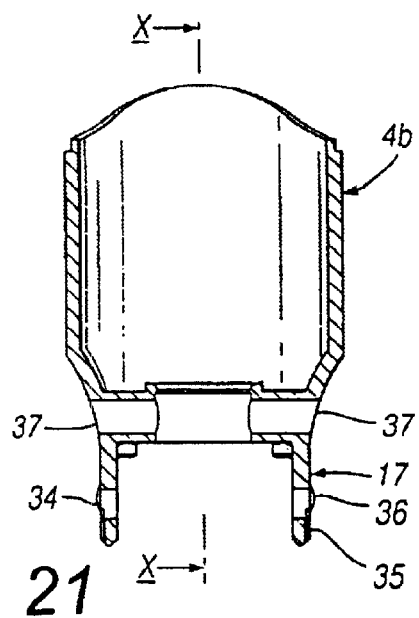
FIG. 21 is a sectional view in direction X—X in FIG. 18.
Figure 23:
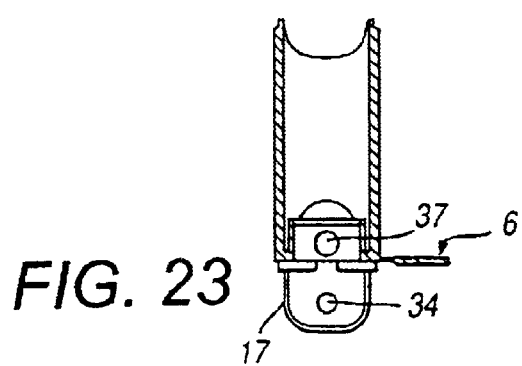
FIG. 23 is a sectional view in direction X—X in FIG. 21.

FIG. 21 is a sectional view in direction X—X in FIG. 18 of the external sleeve 4b. In this view, by-pass holes 37 can be seen which align with the by-pass holes 24 in the suction tube body 4a. FIG. 23 is a sectional view in direction X—X in FIG. 21 and depicts the internal surface of a guide arm 17. An enlarged view of the fixed connection 27 of the resilient strip 6 to the external sleeve 4b appears in FIG. 22.

Figure 24:
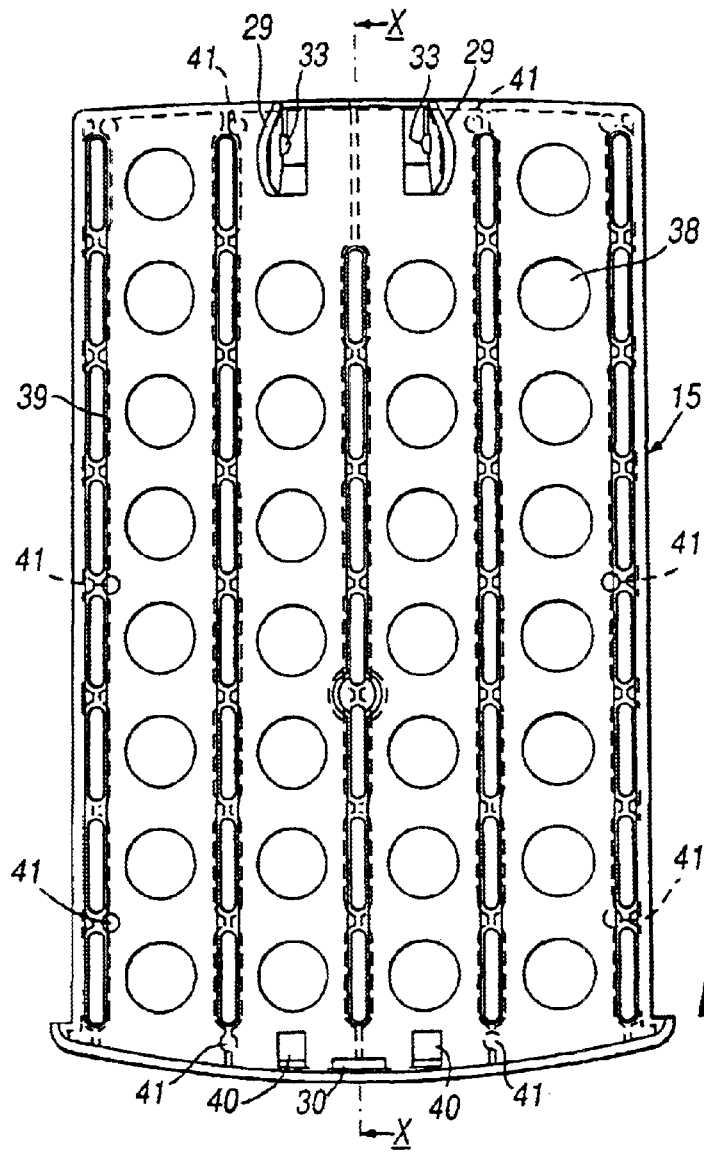
FIG. 24 is a plan view of the upper tray of the carrier.
Figure 25:
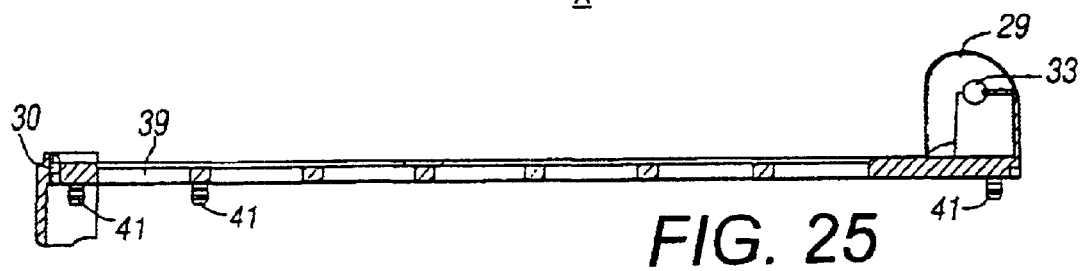
FIG. 25 is a sectional view in direction X—X in FIG. 24.
Figure 26:
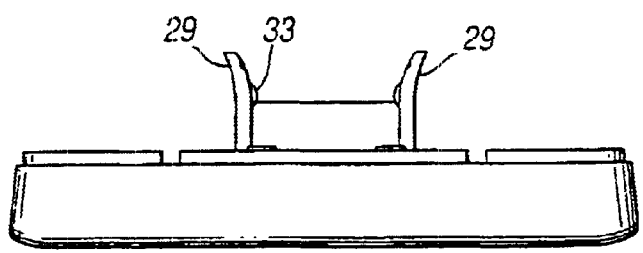
FIG. 26 is a view in direction A in FIG. 24.

FIGS. 24 to 26 depict the upper tray 15 of the carrier 14. In plan view the rows of holes 38 and slots 39 are visible which are configured to align with corresponding blisters 13 and slits 21 in the blister pack 12 (see FIG. 7).

The hook 28 on the resilient strip 6 is intended to be a push-fit into the recess 30 when the inhalation device is assembled. The arrow-shape prevents removal of the hook 28 once pushed into the recess 30 thereby ensuring that the suction tube 4 remains connected to the blister pack assembly 5. For details of the hook 28 reference should be made to FIGS. 38 and 39 described later However, the recess 30 will allow a twisting and sideways movement of the hook 28 which is necessary to ensure that the suction tube 4 can penetrate all the blisters 13 without restriction of movement, in particular, when reaching the blisters which lie at the end of the blister pack 12 where the hook 28 is held. The twisting movement of hook 28 occurs due to the provision of a rib 48 (see FIGS. 38 and 39) against which the hook 28 bears, twisting about the point of contact. On each side of the recess 30 is a locking slot 40 which cooperates with the push-button locking mechanism 3 on the outer case 2. FIG. 25 is a sectional view in direction X—X in FIG. 24 whereas FIG. 26 is a view in direction A in FIG. 24.

The slots 39 are spaced such that the guide arms 17 on the suction tube 4 can penetrate easily. However, the buttons 36 on the guide arms 17 are a snap-fit in the slots 39 to ensure that the suction tube 4 will remain correctly located once a blister 13 has been penetrated by the cutting blade 25 and plunger blades 26 (see FIGS. 31 to 37).

Reference should now be made to FIGS. 27 to 30 which depict the lower tray 16. The lower tray 16 is constructed such that it can lock into position with the upper tray 15 when the blister pack 12 has been inserted. A plurality of guide pins 41 spaced around the perimeter of the upper tray 15 are a snap-fit in corresponding sleeves 42 in the lower tray 16.

Figure 28:
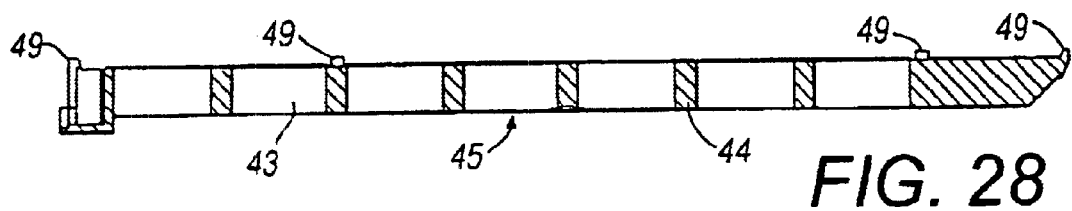
FIG. 28 is a sectional view in direction X—X in FIG. 27.

The lower tray 16 is provided with slots 43 which correspond with the slots 39 in the upper tray 15 and slits 21 in the blister pack 12. The guide arms 17 will enter slots 43 after penetrating the foil layer 20 and lower base 18 of the blister pack 12. In FIG. 28 it is clear that the slots 43 have a depth provided by a wall 44 around the slot extending from the surface 45 of the lower tray 16. The wall 44 ensures that a guide arm 17 will enter the slot 39 in the upper tray 15 correctly and that the suction tube 4 remains upright in the carrier 14 during inhalation of the powdered medicament by the user. By provision of the slots 43 in the lower tray 16, the depth of the lower tray 16 can be less than if the lower tray was solid, in which case, the depth would have to increase by the thickness of the base material of the lower tray 16. Clearly, any constructional feature which reduces the size of the inhalation device or the weight makes the device more advantageous and user-friendly.

Figure 27:
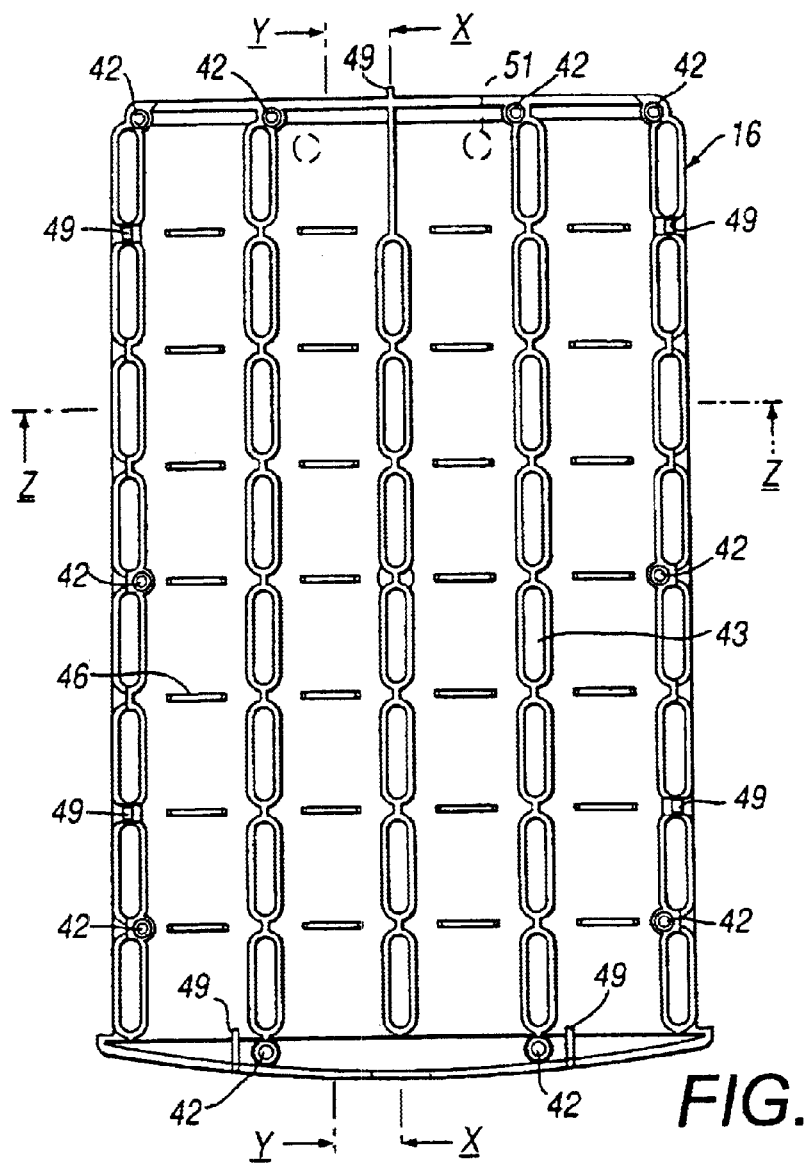
FIG. 27 is a plan view of the lower tray of the carrier.
Figure 29:
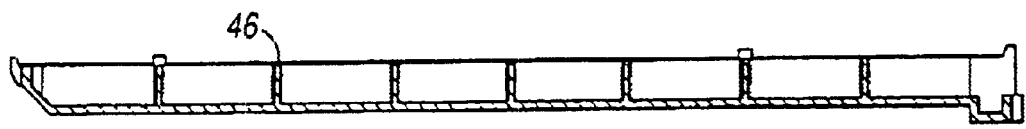
FIG. 29 is a sectional view in direction Y—Y in FIG. 27.

In FIG. 29, which is a sectional view in direction Y—Y in FIG. 27, the upright ridges 46 which help to locate the blister pack 12 correctly can be seen. However, the ridges 46 also provide support for the blister pack 12 when the suction tube 4 penetrates a blister 13. Each blister 13 will sit between two ridges 46 thereby ensuring that the blister pack 12 does not slip within the carrier 14 during assembly. The connection of the upper tray 15 to the lower tray 16 is achieved by interlocking pins 41 (visible in FIGS. 24 and 25) and sleeves 42 (visible in FIG. 27). In this respect, reference should be made to the blister pack 12 in FIG. 5 which is provided with "U" shaped recesses 47 which sit around the interlocking pins 41 and sleeves 42 when the blister pack 12 is assembled between the upper tray 15 and lower tray 16.

The lower tray 16 is also provided with guide pins 49 which ensure accurate location of the blister pack 12 within the lower tray 16. During assembly, the blister pack 12 will typically be placed in the lower tray 16 first so that it is important to locate the blister pack 12 correctly thereby making the next step of assembling the upper tray 15 on the lower tray 16 relatively trouble-free.

In a preferred embodiment, the guide pins 49 could have a hooked configuration to hold the blister pack 12 as well as provide a means for its accurate location.

Figure 30:
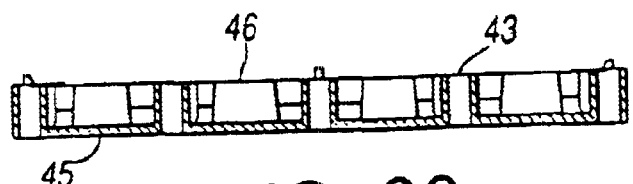
FIG. 30 is a sectional view in direction Z—Z in FIG. 27.

FIG. 30 is a sectional view in direction Z—Z in FIG. 27, showing details of the slots 43 and ridges 46.

FIGS. 31 to 37 depict the inhalation device in use when the suction tube 4 has penetrated a blister 13.

Figure 31:
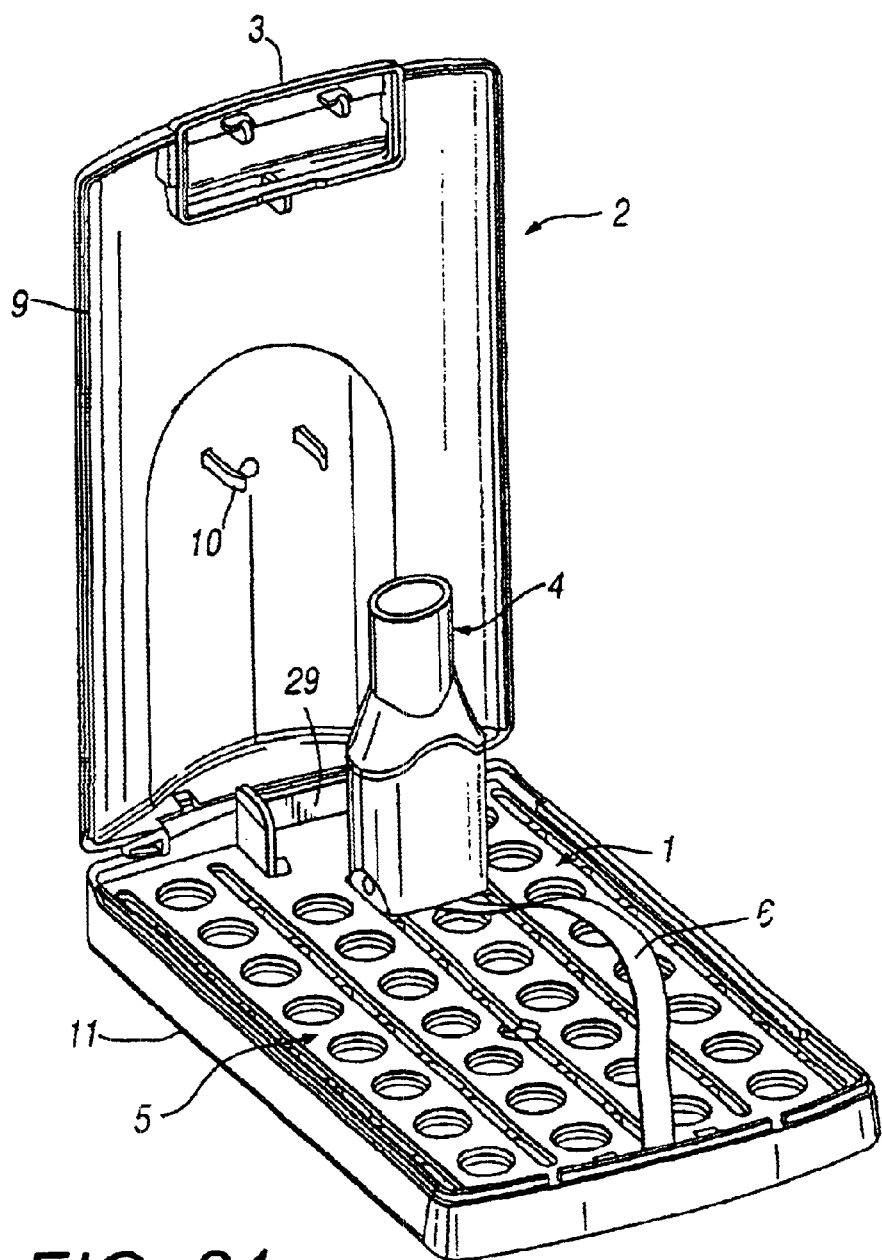
FIGS. 31 to 37 are various views of the inhalation device when the suction tube has been inserted into a blister in the blister pack assembly.
Figure 32:
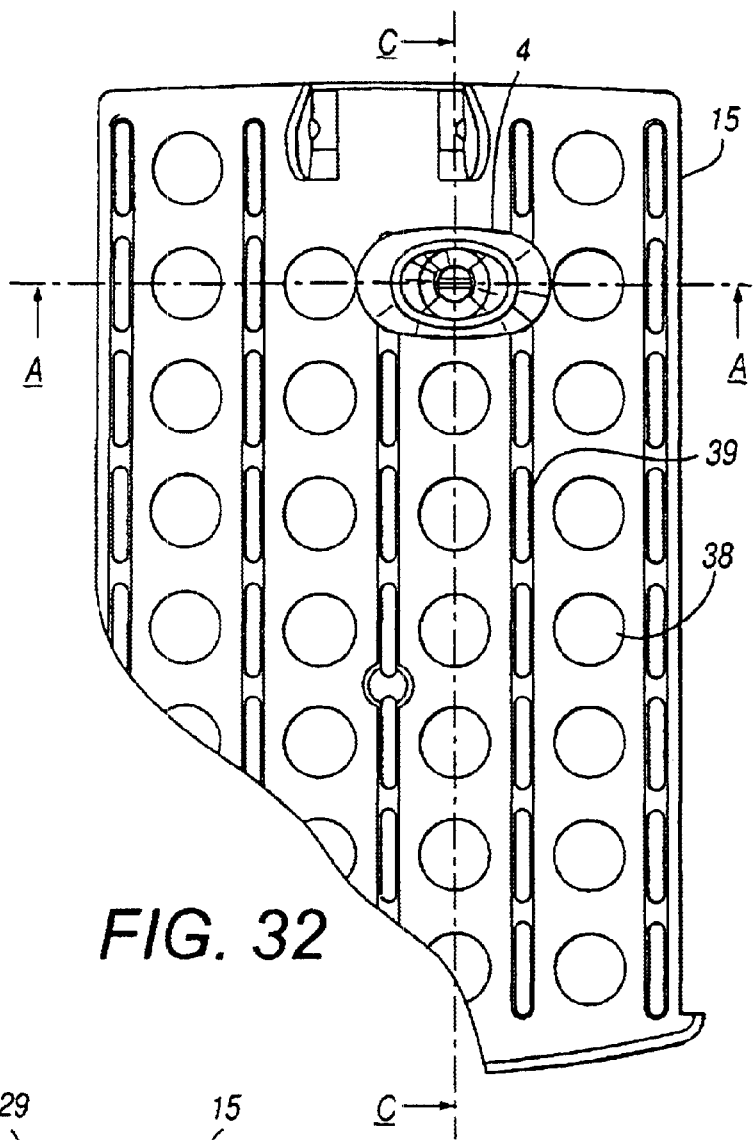

FIG. 31 is a perspective view of the inhalation device when the suction tube 4 has been inserted in the first blister 13 in the second row from the right of the blister pack 12. The resilient strip 6 now serves the function of ensuring that the suction tube 4 remains connected to the blister pack assembly 5. FIG. 32 is a partial plan view of the upper tray 15 with the suction tube 4 inserted in one of the holes 38 and adjacent slots 39. In the enlarged view in FIG. 33, further details are visible of the mouthpiece of the suction tube 4 and through the suction tube 4 down to the cutting blade 25.

Figure 33:
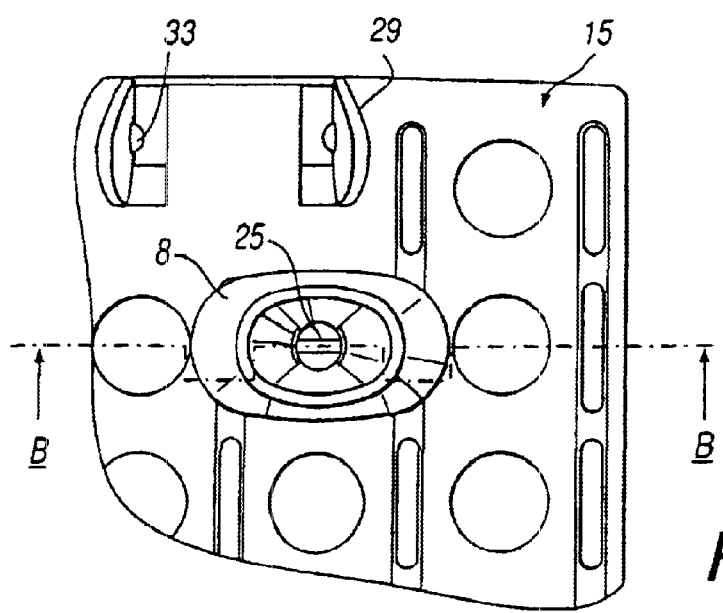
Figure 34:
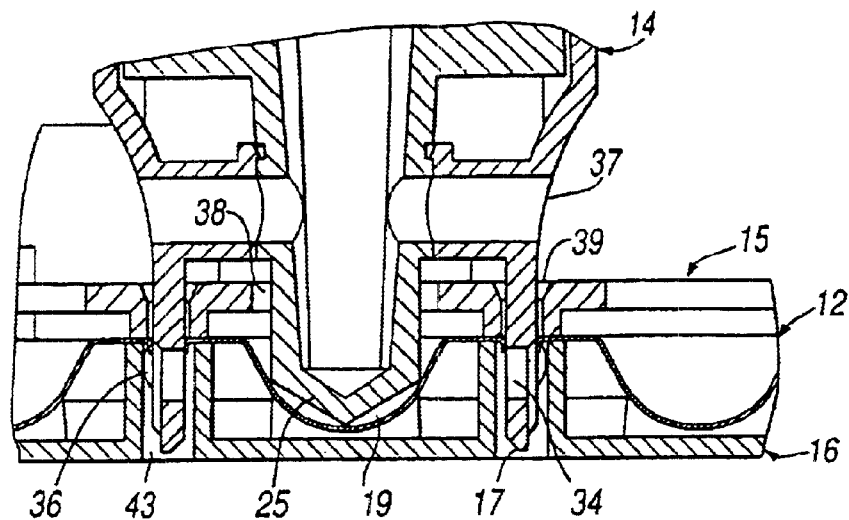
Figure 35:
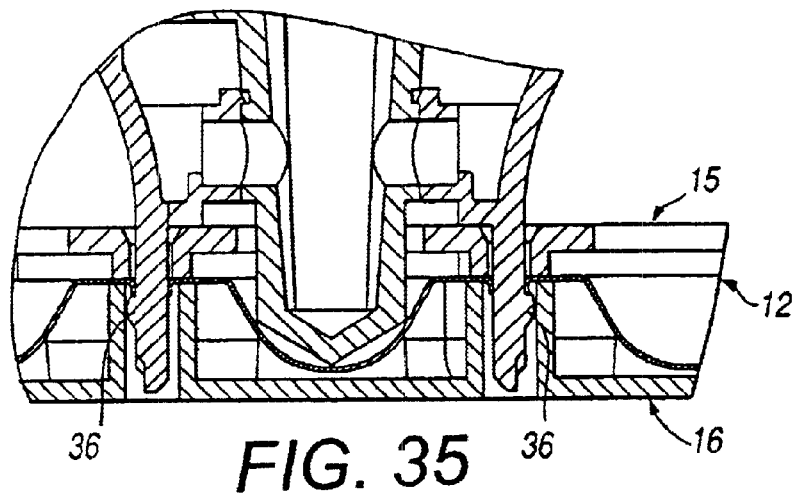
Figure 36:
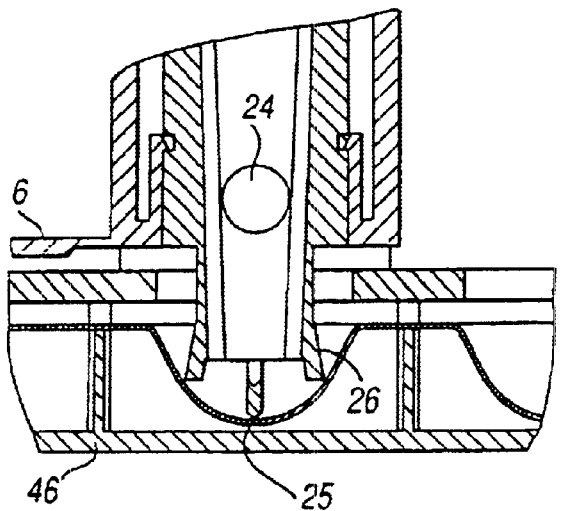
Figure 37:
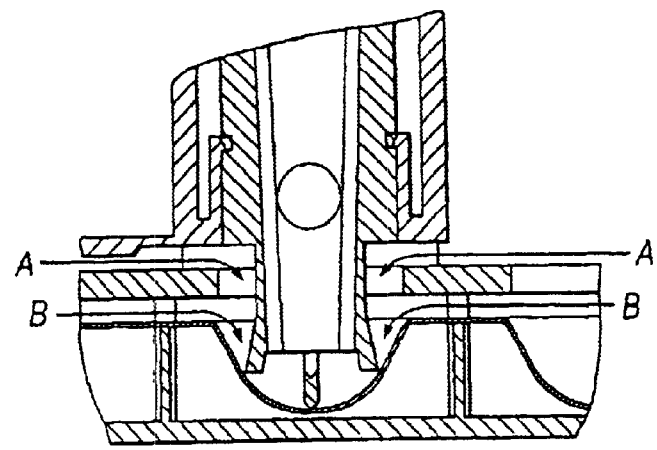

FIGS. 34, 35 and 36 are different sectional views in directions A—A, B—B and C—C respectively in FIGS. 32 and 33. The sectional views show clearly how the suction tube 4 penetrates the upper tray 15, the blister pack 12 and the lower tray 16. FIG. 37 depicts the air flow into the inhalation device when a user inhales to empty the contents of the cavity 19 and corresponds to FIG. 36.

In FIGS. 34 and 35, it is clear how the buttons 36 on the guide arms 17 snap into the upper tray 15 and the lower tray 16 to ensure that the suction tube 4 remains correctly located during inhalation through the mouthpiece by a user. After inhalation the suction tube 4 can be removed simply by overcoming the slight resistance of the buttons 36 when locked in the slots 43.

It is also important to note that the suction tube 4 is constructed such that when a blister 13 is penetrated, there is an air gap between the suction tube 4 and the surface of the upper tray 15 which allows an air flow A (see FIG. 37). The distal end 7 of the suction tube 4 which comprises the cutting mechanism 22 is also constructed such that during penetration of a blister 13, there will be an air gap between the cutting mechanism 22 and the perimeter of the hole 38 in the upper tray 15. Furthermore, the blister pack assembly 5 is constructed such that there is an air gap between the lower surface of the upper tray 15 and the blister pack 12 which allows an air flow B (see FIG. 37). The air flow A and air flow B into the cavity 19 facilitate inhalation of the contents by a user.

Figure 38:
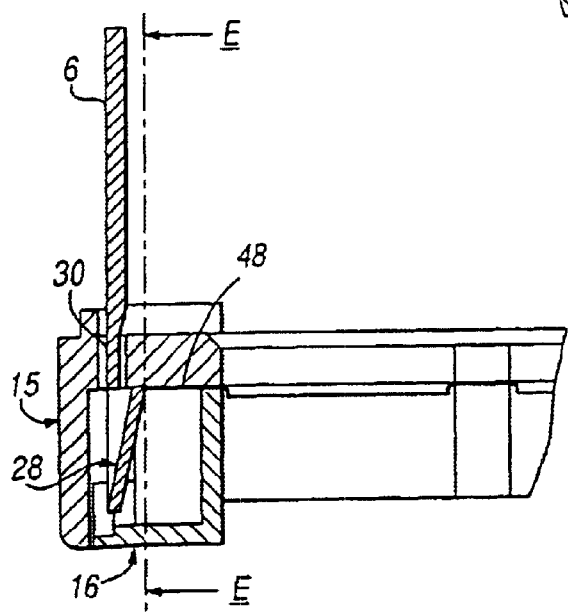
FIGS. 38 and 39 depict detail of the hook on the resilient strip.
Figure 39:
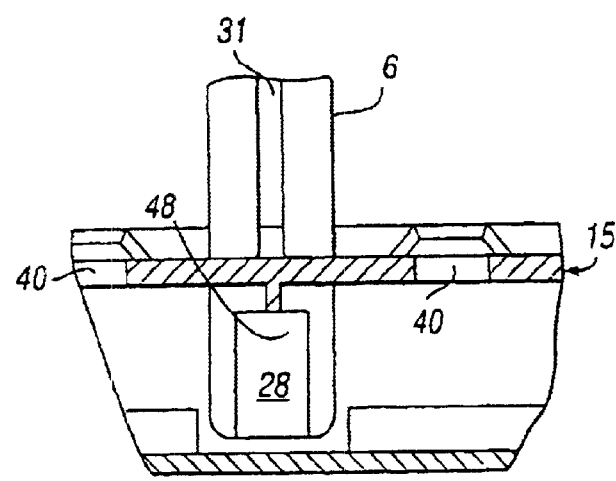

FIGS. 38 and 39 show enlarged detail of the arrow-shaped hook 28 on the resilient strip 6 when located in the blister pack assembly 5. FIG. 38 is a sectional view which depicts how the hook 28 is held in the recess 30.

In FIG. 39, which is a view in direction E in FIG. 38, the hook 28 is seen to be held just below the upper tray 15. However, as mentioned earlier the hook 28 is able to move within the recess 30 from side to side and twist as the suction tube 4 moves from blister to blister. The twisting movement is achieved by a rib 48 against which the hook 28 bears, rotating about the point of contact.

Figure 40:
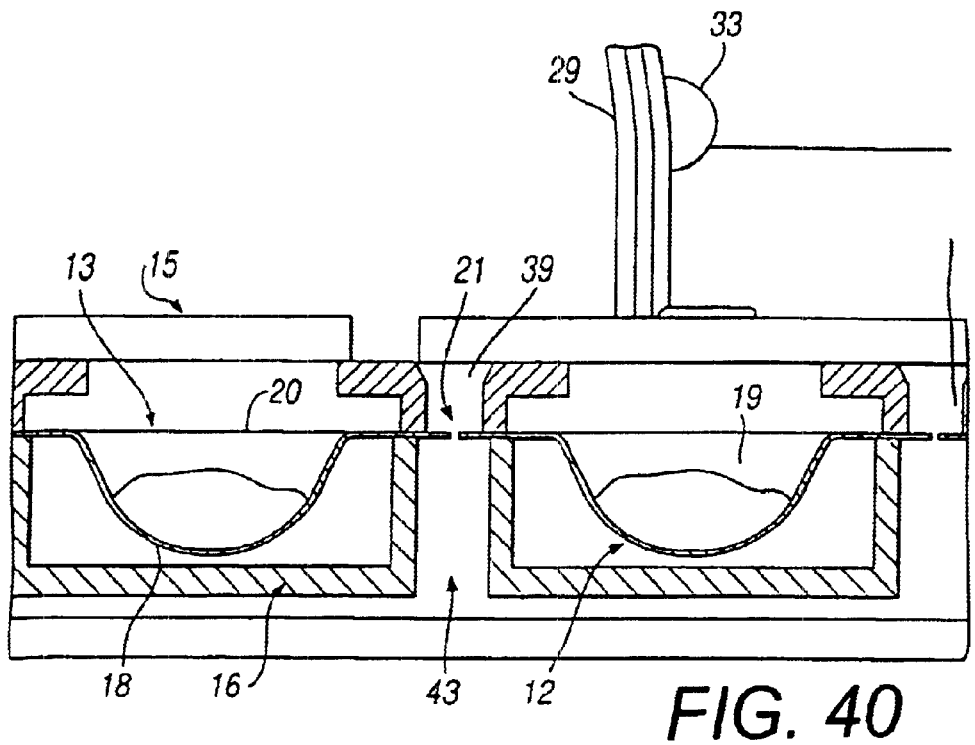
FIG. 40 is an enlarged view of the blister pack assembly.

FIG. 40 is an enlarged sectional view through the blister pack assembly 5 which shows how the blister pack 12 sits between the upper tray 15 and lower tray 16. The slit 21 has been formed by scoring the foil layer 20 and lower base 18.

Figure 41:
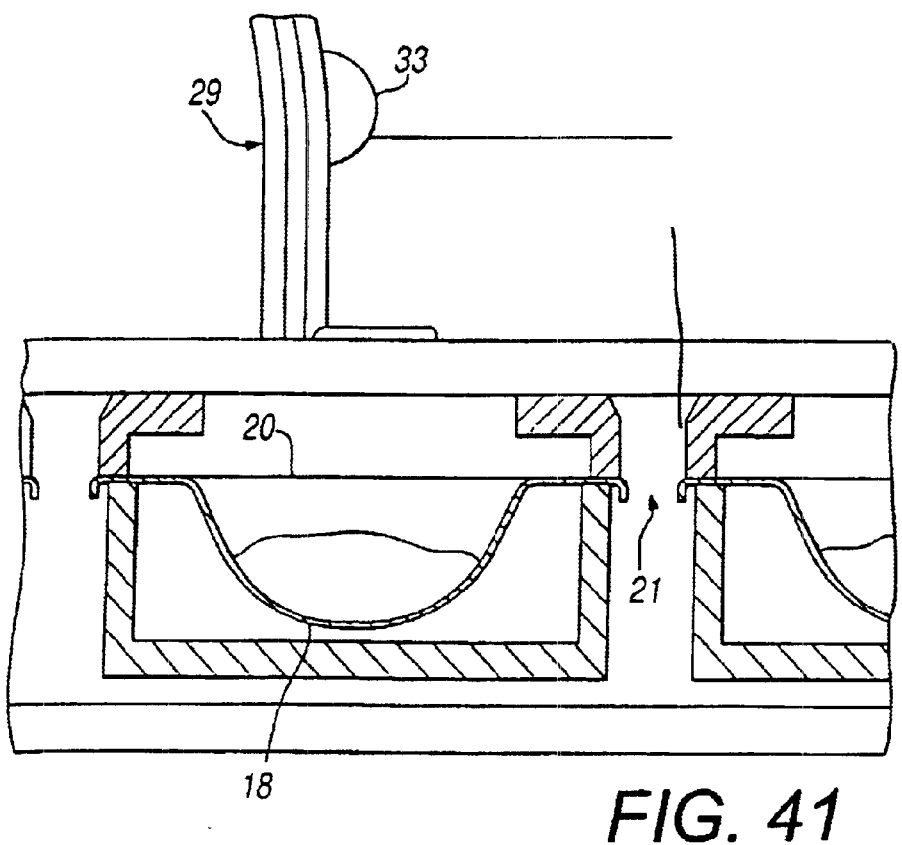
FIG. 41 is an enlarged view of an alternative blister pack assembly.
Figure 42:
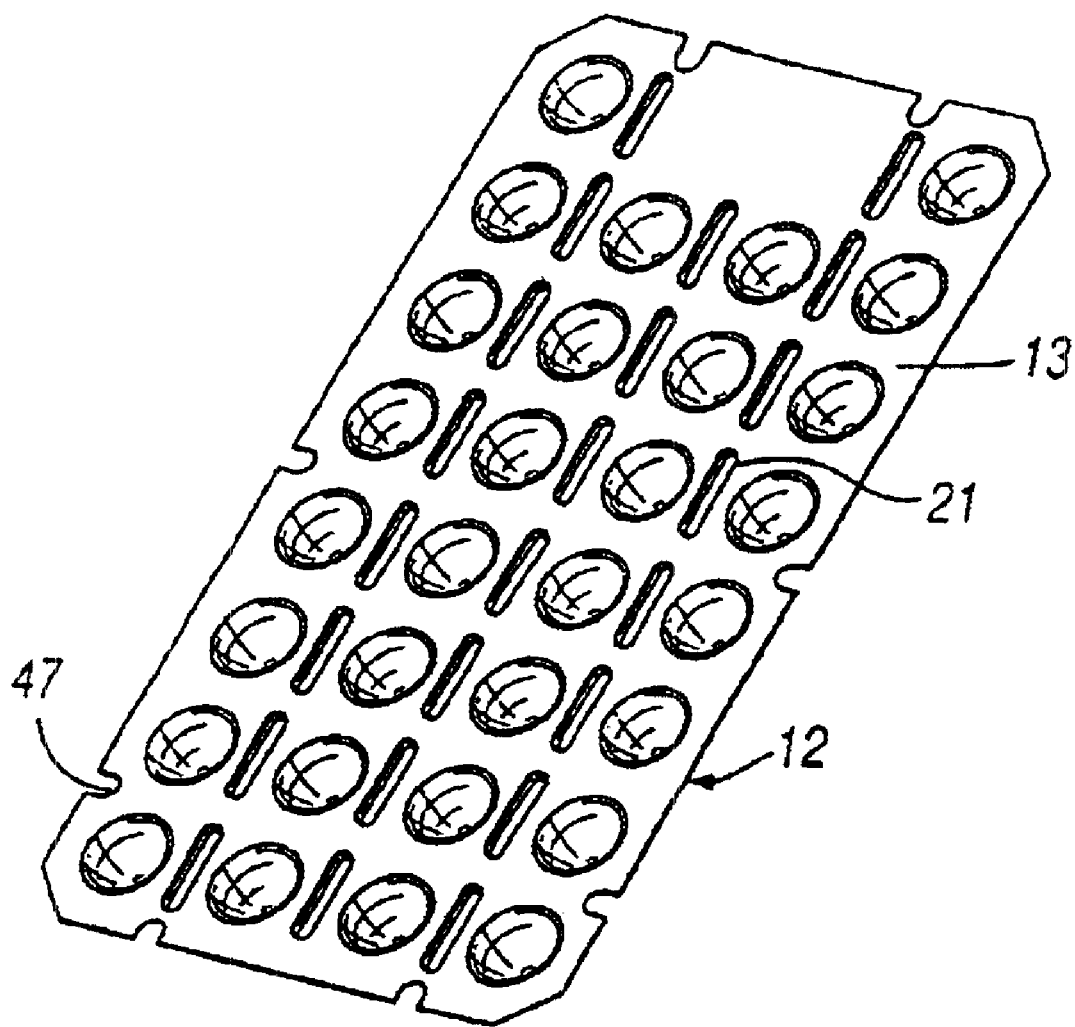
FIG. 42 is a plan view of the blister pack in FIG. 41.

In FIG. 41, an alternative blister pack 12 is depicted where the slits 21 have been folded or pushed downwards making the slit wider without affecting the minimum optimum sealing distance described earlier. With the folded slits 21, penetration of the blister pack 12 by the guide arms 17 is made easier. FIG. 42 is a perspective view of just the blister pack 12 in FIG. 41 depicting the folded slits 21.

What is claimed is:

1. A blister pack having a plurality of blisters each holding a dose of a powdered medicament comprising a lower base containing a plurality of cavities for the powdered medicament and an upper sealing foil layer which covers the lower base to form the blisters, wherein each cavity is provided with at least one adjacent slit formed by scoring the foil layer and lower base, the slit cooperating with a respective guide arm on a suction tube to ensure accurate penetration of a cavity by a suction tube through which a user can inhale said dose in said cavity.

2. A blister pack as claimed in claim 1, wherein each said slit has opposed edges and the opposed edges of said slit are folded back towards the lower base to facilitate penetration by the suction tube.

3. A blister pack as claimed in claim 1 or claim 2, wherein a scored slit sits at a distance of approximately 2 mm from the cavity perimeter.

4. A blister pack assembly comprising a blister pack having a plurality of blisters each holding a dose of a powdered medicament comprising a lower base containing a plurality of cavities for the powdered medicament and an upper sealing foil layer which coven the lower base to form the blisters, wherein each cavity is provided with at least one adjacent slit formed by scoring the foil layer and lower base, the slit cooperating with a respective guide and on a suction tube to ensure accurate penetration of a cavity by a suction tube through which a user can inhale said dose in said cavity, and a carrier for the blister pack.

5. A blister pack assembly as claimed in claim 4, wherein said cavities and said slits in said blister pack are located at respective positions, and wherein the carrier comprises an upper tray and a lower tray which are interconnectable around the blister pack, the upper tray being provided with a plurality of holes and slots which sit above and correspond with the positions of the cavities and slits in the blister pack.

6. A blister pack assembly as claimed in claim 5, wherein the lower tray is provided with a plurality of slots, each said slot sitting below and corresponding with a respective said slit in the blister pack.

7. An inhalation device comprising a blister pack assembly comprising
a blister pack having a plurality of blisters each holding a dose of a powdered medicament comprising a lower base containing a plurality of cavities for the powdered medicament and an upper sealing foil layer which covers the lower base to form the blisters, wherein each cavity is provided with at least one adjacent slit formed by scoring the foil layer and lower base, the slit cooperating with a respective guide arm on a suction tube to ensure accurate penetration of a cavity by a suction tube through which a user can inhale said dose in said cavity, and
a carrier for the blister pack, and
a suction tube which is constructed for cooperation with the blister pack assembly having a distal end which can penetrate the foil above a cavity a proximal end through which the user inhales and at least one guide arm which accurately locates the distal end of the suction tube in a cavity by penetrating the blister pack assembly.

8. An inhalation device as claimed in claim 7, wherein the guide arm or arms have a tapered configuration to facilitate location in the blister pack assembly.

9. An inhalation device as claimed in claim 7 or claim 8, wherein the suction tube is removably hinged to the carrier by way of cooperating elements on the guide arm or arms and the carrier.

10. An inhalation device as claimed in claim 9, wherein the guide arm or arms are provided with a shallow channel which facilitates relocation of the suction tube on the cooperating elements.

11. An inhalation device as claimed in any of claims 7 to 10, wherein the distal end of the suction tube is constructed to ensure there is an air gap between the suction tube and the blister pack assembly when the suction tube penetrates a blister.

* * * * *